United States Patent [19]

Ball

[11] Patent Number: 5,696,315
[45] Date of Patent: *Dec. 9, 1997

[54] METHOD AND APPARATUS FOR MEASURING VISCOSITY

[75] Inventor: Dean M. Ball, Gainesville, Ga.

[73] Assignee: Cannon Instrument Company, State College, Pa.

[*] Notice: The term of this patent shall not extend beyond the expiration date of Pat. No. 5,616,855.

[21] Appl. No.: 724,860

[22] Filed: Oct. 3, 1996

Related U.S. Application Data

[63] Continuation-in-part of Ser. No. 544,863, Oct. 18, 1995.
[51] Int. Cl.$^6$ .............. G01N 11/04; G01N 35/16
[52] U.S. Cl. ............... 73/54.43; 73/864.81
[58] Field of Search ............... 73/54.01, 54.04, 73/54.07, 54.43, 864.21, 864.23, 864.24, 864.73, 864.74, 864.81

[56] References Cited

U.S. PATENT DOCUMENTS

| | | | |
|---|---|---|---|
| 1,549,898 | 8/1925 | Bader | 73/54.43 X |
| 2,227,938 | 1/1941 | Krebs | 73/54.43 X |
| 3,071,961 | 1/1963 | Heigl et al. | 73/54.08 |
| 3,798,960 | 3/1974 | Glass | 73/54.05 |
| 4,530,234 | 7/1985 | Cullick et al. | 73/23.35 X |

*Primary Examiner*—Michael Brock
*Attorney, Agent, or Firm*—Seidel, Gonda, Lavorgna & Monaco, P.C.

[57] ABSTRACT

An apparatus for measuring viscosity of liquids includes an external chamber (10) which encloses an internal chamber/duct (20) having an inlet (21) and an outlet (22). Internal chamber (20) houses a fan (30) for forcing air through the duct, a first heater (40) for heating air within the duct, a second heater (81/82) for heating air externally of the duct, a thermal ballast (50) for maintaining the temperature of the air in the duct constant, and a viscometer (72) for measuring viscosity of liquids.

14 Claims, 4 Drawing Sheets

5,696,315

METHOD AND APPARATUS FOR MEASURING VISCOSITY

REFERENCE TO RELATED APPLICATION

This is a continuation in part of application Ser. No. 08/544,863, filed Oct. 18, 1995.

TECHNICAL FIELD

The present invention relates to methods and apparatuses for measuring the viscosity of liquids.

BACKGROUND OF THE INVENTION

Viscosity measurement of liquids is an essential tool used in the characterization of many products. For instance, the suitability of lubricating oils for a particular purpose is closely related to viscosity and to the variation of viscosity with temperature. Most polymers, including nylon, polyester, rubber, polyethylene, cellulose, polyvinylchloride, and polystyrene are routinely characterized during production by dissolving them in a suitable solvent and then measuring the viscosity of the resulting solution.

The viscosity of liquids is strongly dependent on temperature. As the temperature of liquid changes, the viscosity also changes. An accurate measurement of viscosity therefore requires accurate and stable temperature control. If viscosity is to be measured to with in an accuracy of 1%, the temperature must be highly controlled.

Measurement of viscosity is often performed in thermostatic baths using a liquid as the thermostatic media. Such baths often have an accuracy of +/−0.01 degrees Celsius. This method relies on the high heat capacity of a liquid to provide a stable temperature environment during viscosity measurement. In the typical viscosity measurement apparatus, a vessel of water or oil is stirred and heated using a highly accurate thermostatic controller. In such a vessel the rate of change of the temperature is low and the viscosity measurement can be performed with relative ease. Liquid baths, however, have several disadvantages. For instance, a liquid bath requires constant maintenance. If water is used as the bath medium, evaporation can pose a problem. Bacterial and algae growth in water necessitates frequent changes of the water media.

When higher temperatures are used, oil is normally chosen as the liquid medium. As the oil becomes hot and starts to oxidize, an objectionable odor is created in the laboratory. Another disadvantage of oil baths is the risk of dripping the oil media onto laboratory surfaces once the viscosity apparatus is removed from the bath. Also, liquid baths are subject to leaks. In the case of hot oil baths, operators are exposed to the dangers of burns in the event that the bath container, which is often glass, is broken.

An additional disadvantage with using a liquid medium as a thermostatic bath arises when the viscosity must be measured at several temperatures. A separate thermostatic bath must then be maintained at each temperature. Due to the high heat capacity of liquid, the time required for changing temperature in a bath is between six to eight hours. Typically, a lubricant laboratory would have three to four liquid baths operating continuously.

It thus is seen that the liquid baths utilized in the prior art as part of viscosity measurement apparatuses require high maintenance and care to operate. Additionally, numerous baths are required to measure a wide range of temperatures.

Accordingly, a need remains for a viscosity measuring apparatus and method which can accommodate a wide range of temperature measurements and yet which is not susceptible to the problems heretofore associated with the liquid bath type apparatuses.

SUMMARY OF THE INVENTION

In a preferred form of the invention, an apparatus for measuring the viscosity of liquids in an ultra stable temperature environment has a thermally insulated test chamber. A support tray for supporting open top containers of liquids to be tested within the chamber is mounted in the chamber. A thermally insulated duct having an inlet and outlet is mounted within the chamber, as is a fan for circulating air through the duct and chamber. A first heater is mounted within the duct for heating air flowing through the duct. A second heater is preferably mounted outside the duct for heating air circulating in the chamber externally of the duct. A viscometer is mounted at least partially within the duct downstream of the heater for measuring the viscosity of liquids in containers supported upon the tray. A thermal ballast of high heat conductivity and high surface area is also preferably mounted in the duct between the heater and viscometer.

As air from the chamber is circulated through the duct, it flows over the heater and the ballast so that the air stream is thermally stable as it passes over the viscometer and test samples. After passing over the test samples, the air is recirculated outside the duct, heated and drawn back into the duct at the fan intake.

DETAILED DESCRIPTION OF THE INVENTION

Figure 1:
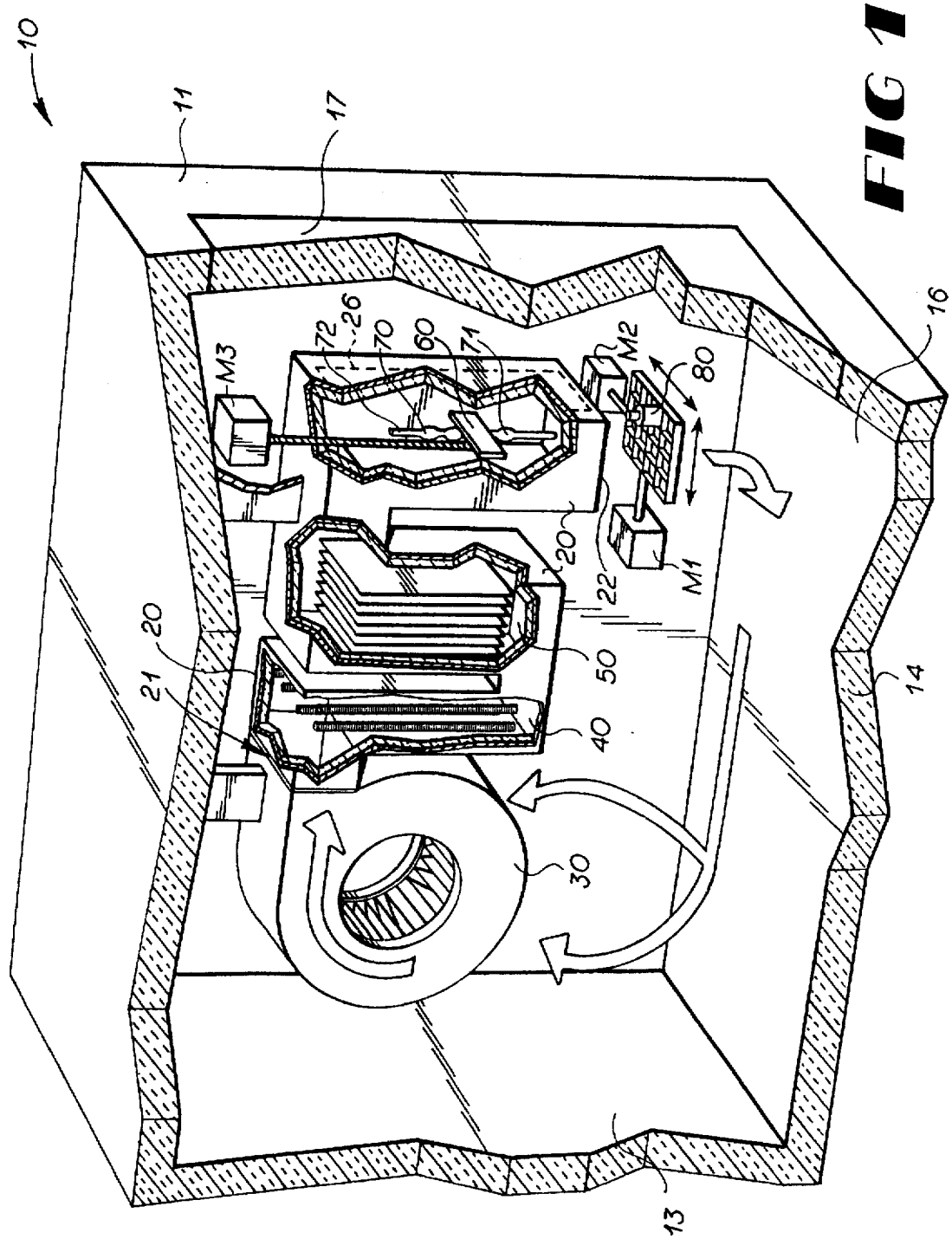
FIG. 1 is a perspective view of an apparatus for measuring viscosity that embodies principles of the invention in a preferred form with a portion shown broken away to reveal internal components.

Referring now to the drawings, an apparatus for measuring viscosity is illustrated in FIG. 1 which has a thermally insulated external chamber 10 having a side wall 11. External chamber 10 is preferably formed of aluminum with an outer polyurethane layer of foam insulation having a thickness of 25 mm. An insulated access door 17 for allowing entry into the interior of external chamber 10 is attached to side wall 11. An internal chamber or duct 20 having an inlet 21 and an outlet 22 is mounted within the external chamber 10 suspended from the chamber top. Internal chamber 20 is formed of aluminum sheeting approximately 3 mm thick with epoxy fiberglass composite insulation. Internal chamber 20 has an access door 26 adjacent to external chamber access door 17.

Figure 2:
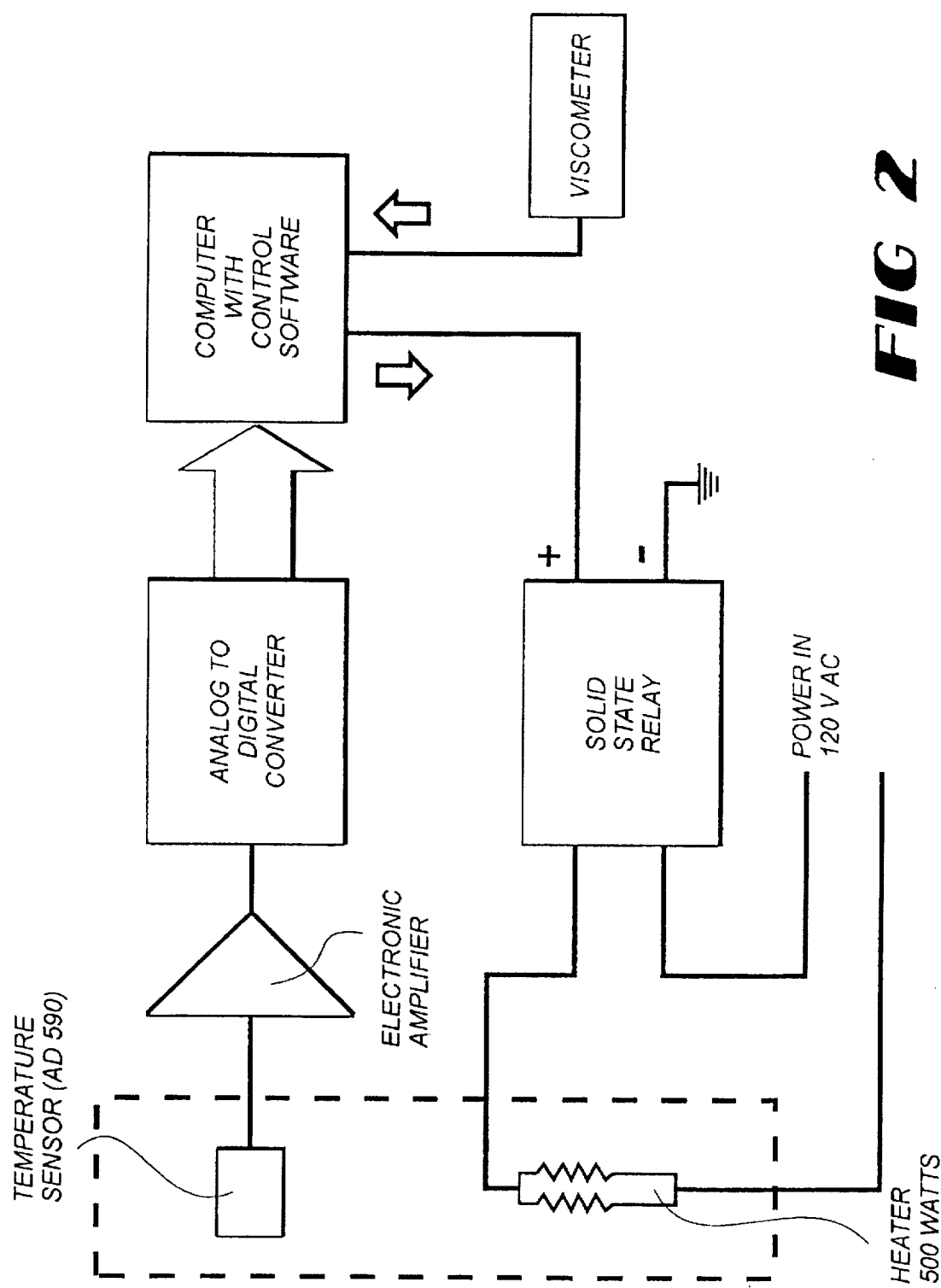
FIG. 2 is a block diagram illustrating the relationship between the temperature sensor, the heating element, and the computer control system of the apparatus of FIG. 1.

A fan 30 is mounted in the external chamber 10 to the inlet 21 of duct 20. An electric heater 40 is mounted in duct 20 downstream from the fan 30, and is connected through a solid state relay to a computer as shown in FIG. 2. A thermal ballast 50 is mounted in the duct between the heater 40 and the duct outlet 22. Thermal ballast 50 is made of a series of thin copper plates 0.5 millimeters thick spaced 3 millimeters apart.

A viscometer 72 and a temperature sensor 60 are mounted in mutual proximity within the duct between the thermal ballast 50 and the duct outlet 22. Viscometer 72 is connected by a threaded drive shaft to a motor M3 for movement of viscometer 72 in a vertical direction. A sample tray 80 is mounted within the duct 20 for movement in a horizontal plane in both X and Y directions below viscometer 72. The sample tray 80 is coupled by unshown means with threaded drive shafts of motors M1 and M2, respectively, which respectively drive the tray in X and Y axes directions. Finally, the duct section that houses the temperature sensor, viscometer and sample tray has a door 26 aligned with the external chamber access door 17.

With reference to FIG. 2, it is seen that the temperature sensor 60 is coupled with the computer through an electronic amplifier and an analog to digital converter. The viscometer 72 is also coupled to the computer. The heater 40 is also controlled by the computer. Although any number of computers may be used, an IBM-PC compatible computer with a 80486 microprocessor is preferred. The internal chamber is preferably aluminum in order to minimize the time required to heat up the chamber to its operating temperature. The fan 30 is a centrifugal type fan with 5 cubic meters of air per minute capacity. The heater 40 comprises a gang of nichrome heater wires having a low mass in the shape of a series of wire turns. The nichrome heater provides for a temperature range between 35 to 150 degrees Celsius. If an external cooler is added to the apparatus, the temperature range can be between −10 and 150 degrees Celsius. That portion of the duct that houses the heater is preferable coated with an epoxy fiberglass composite to achieve insulative effect as well as to secure the wiring connections. The thermal ballast 50 is made of material that has high heat conductivity such as silver, iron, aluminum or copper. The ballast is shaped to have a high surface area generally uniformly. Given this factor, the shape selected may be a series of adjacent parallel plates as seen in FIG. 1, or as a gang of spirals, or in filamentous wool forms.

The viscometer 72 may be one of the conventional single capillary bulb type. In the preferred embodiment though, the viscometer has two viscosity measuring bulbs, namely a lower capillary and measuring bulb 71, and an upper, double capillary and measuring bulb 70.

A viscometer of the double bulb type provides for a more extended viscosity measurement range. Once its lower bulb is filled and raised, the viscosity of the sample in the bulb is measured as it gravitates back into a container. Sample detection is made with fiber optic cables using an infrared light source. The computer monitors the data generated by the viscometer and calculates viscosity utilizing conventional calculation software. In the dual bulb type viscometer, as a sample is drawn into its lower bulb, pressure and time are recorded by the computer. If the time-pressure product is low, the sample is drawn further into the upper capillary. Conversely, if the time-pressure product is high, the sample is released through the lower capillary back into the container. The dual type viscometer allows for the measurement of viscosity over a range of 1 to 100 centistokes. By changing viscometers the entire range of viscosity from 0.3 to 30,000 centistokes can be analyzed.

In operation, access doors 17 and 26 are opened. The samples are placed in disposable vials which are loaded onto tray 80 in individual checkerboard arrayed receptacles or indentations along the tray top. For the testing of more volatile liquids the vials are covered with aluminum foil to inhibit evaporation once the access doors are closed and the chamber is heated. Access doors 17 and 26 are then closed and the computer activated which energizes the heater and fan. Once the desired chamber temperature is achieved, the heater is activated intermittently by the computer in order to maintain the preselected temperature level. The air temperature within the apparatus can be changed from 40 degrees Celsius to 100 degrees Celsius in approximately 16 to 18 minutes.

Downstream of the ballast the air temperature is continuously measured by the temperature sensor 60 and monitored by the computer. After the air stream in the duct passes over viscometer and temperature sensor, it is returned outside of the duct to the intake of the fan 30 to complete a cycle.

Movement of the viscometer is controlled by the computer in synchronous with movements of the tray. The viscometer is lowered by motor M3 causing it to puncture the foil cover and enter into the vial directly beneath it and its sample liquid. The sample is then drawn into the viscometer and its viscosity measured. Each time this is done the viscometer is cleansed by an unshown cleaning device and solvent. The tray 80 is then indexed so as to bring another vial into position directly beneath the viscometer. The viscometer is then driven down into that vial, again puncturing the aluminum foil, and the process repeated until all of the vial samples have been tested and the viscosity measurement for each vial recorded.

EXAMPLE

The apparatus of FIG. 1 and 2 was tested with a thermal ballast 50 consisting of 32 sheets of copper each having a dimension of 8 cm×23 cm by 0.5 cm. The total mass of the copper used was about 2.5 kg and the total surface area exposed to the air stream about 11,776 sq. cm. Twelve samples were tested. During the period of time in which the samples were tested, the temperature was found not to vary more than 0.01 degrees Celsius. As shown in Table A, viscosity percent deviation from the average was maintained at a low level. Notwithstanding movement of the tray and samples, and the puncturing of foil under these conditions, this did not distract from the effectiveness of the apparatus, in maintaining a highly thermally stable environment.

TABLE A

| Sample (Position | Viscosity (Centistoke) | % Deviation From Average |
|---|---|---|
| A | 37.23 | +0.05 |
| B | 37.17 | −0.11 |
| C | 37.23 | +0.05 |
| D | 37.09 | −0.34 |
| E | 37.15 | −0.16 |
| F | 37.33 | +0.32 |
| G | 37.22 | +0.03 |
| H | 37.16 | −0.13 |
| I | 37.28 | +0.19 |
| J | 37.23 | +0.05 |
| K | 37.30 | +0.24 |
| L | 37.11 | −0.27 |

Average 37.21 Max % Deviation: +0.32, −0.27

Figure 3:
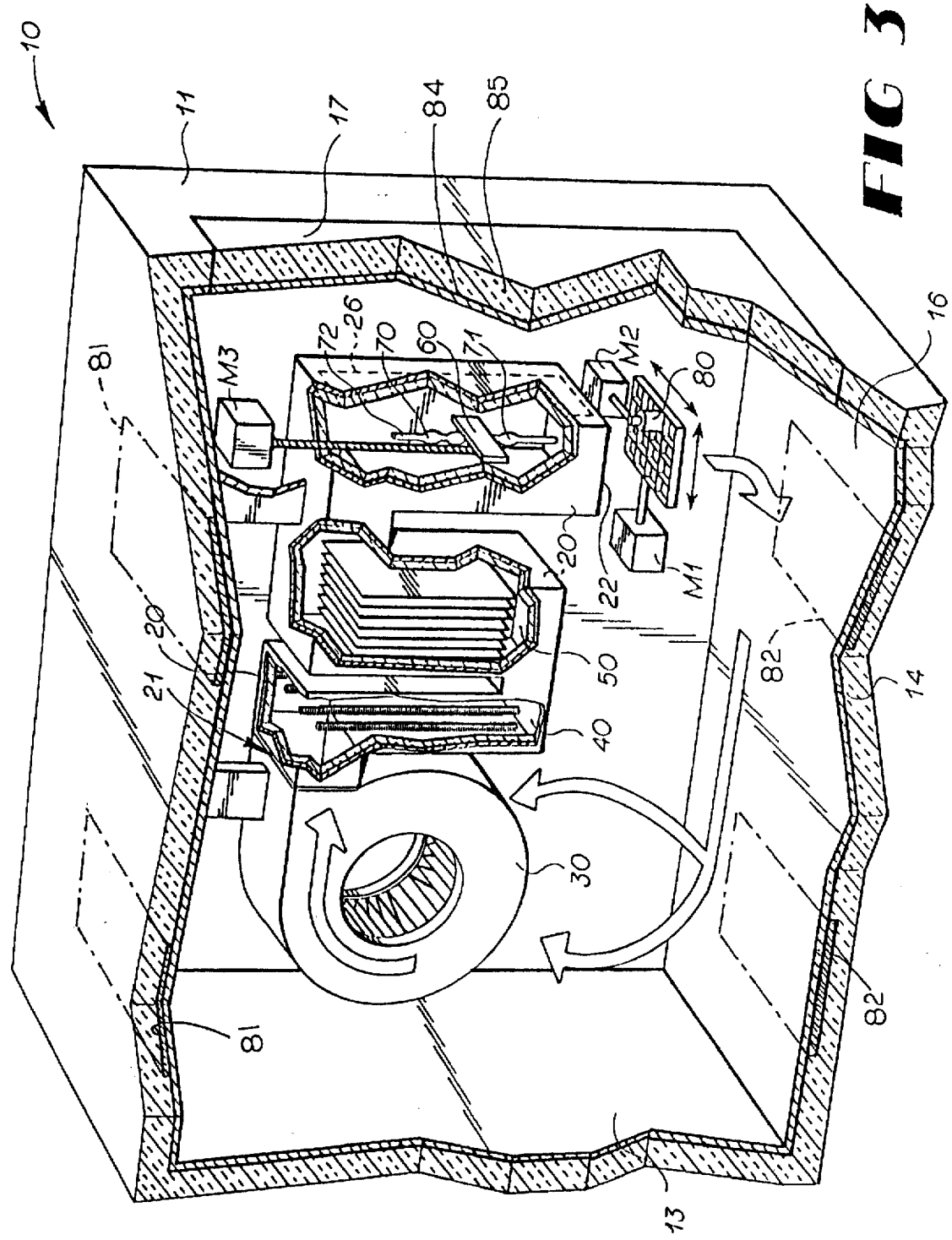
FIG. 3 is a perspective view of an apparatus for measuring viscosity that embodies principles of the invention in another preferred form with a portion shown broken away to reveal internal components.
Figure 4:
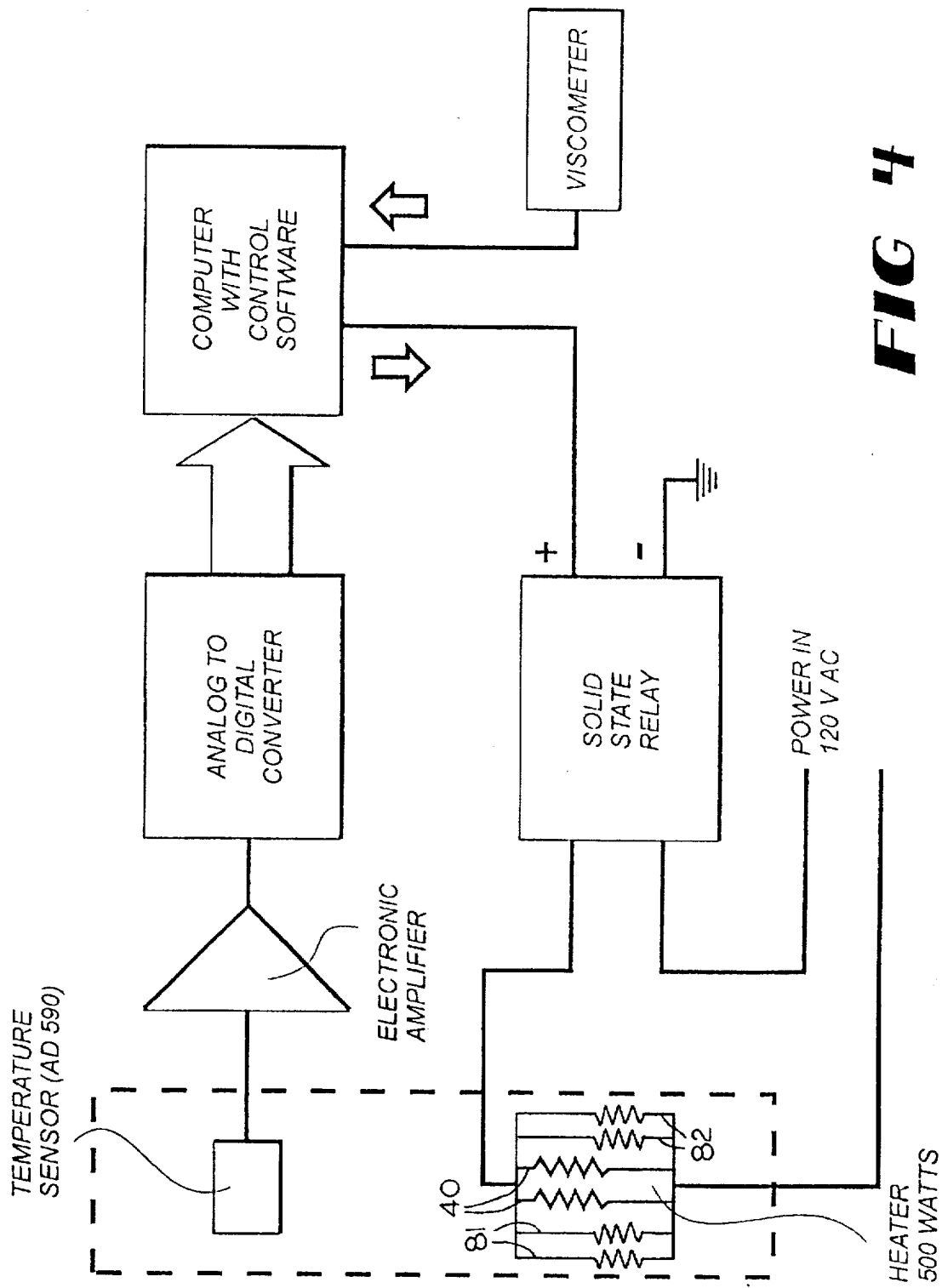
FIG. 4 is a block diagram illustrating the relationship between the temperature sensor, the heating elements, and the computer control system of the apparatus of FIG. 3.

Referring next to FIGS. 3 and 4, an apparatus for measuring viscosity in another preferred form is shown. Here, the apparatus is essentially the same as that previously described except for the addition of a second heater. The second heater has two 100 watt heating elements 81 embedded within the top wall of the external chamber 10 and two 100 watt heating elements 82 embedded within the bottom wall of the external chamber 10. Preferably, heating elements 81 and 82 have a serpentine metallic wire mounted within a silicon rubber bed. Heating elements 81 and 82 are positioned between the aluminum shell 84 and the outer insulative foam layer 85. Hence, the elements are in thermal communication with the interior of chamber 10 through the highly thermally conductive aluminum shell. Preferably, heater 40 here also employs a 100 watt element.

It has been discovered that the addition of the second heater 80 provides a more stable or consistent temperature variation within the interior of the external chamber. Furthermore, the second heater provides a more stable and consistent temperature differential between the top of the viscometer and the bottom of the viscometer. For example, when operating the apparatus with an internal temperature of 100 degrees Celsius the temperature difference between the top and bottom of the viscometer varies approximately 0.07 degrees Celsius and the temperature difference at the four corners of the chamber is as much as 3 degrees Celsius below the operating temperature of 100 degrees Celsius. However, when operating the apparatus with the additional heater 80 the temperature difference between the top and bottom of the viscometer is reduced to 0.02 degrees Celsius and the temperature difference at the corners is reduced to 0.5 degrees Celsius. This modification provides for a more precise measurement of viscosity. The deviation of viscosity from the average viscosity of several samples using only heater 40 was found to be +0.32 and −0.27 percent, while with the deviation in the apparatus using second heater 80 was found to be +0.15 and −0.15.

Again, preferably the heating elements of the second heater are mounted within the top wall and bottom wall of the external chamber. However, these heating elements may alternatively or additionally be mounted to the side walls of the external chamber. Also, it is preferred that the heating elements 81 and 82 are mounted on the external side of the aluminum shell. However, it is also contemplated that with proper dispersement of the heat produced therefrom these heating elements may alternatively be mounted within the external chamber 10.

It thus is seen that a viscosity measuring apparatus and method are now provided which allow for the measurement of viscosity in an extremely thermally stable environment and yet which can accommodate a wide range of temperatures measured. Not being a liquid bath type, it avoids problems previously associated with such viscosity measuring apparatus. Though the apparatus and method has been shown and described in its preferred form, many modifications, additions, and deletions may be made thereto without departing from the spirit and scope of the invention as set forth in the following claims.

I claim:

1. Apparatus for measuring the viscosity of liquids in an ultra stable temperature environment which comprises a thermally insulated test chamber, support means for supporting containers of liquids to be tested within said chamber, a thermally insulated duct mounted within said chamber, means for circulating air within said chamber through said duct, first heater means mounted within said duct for heating air flowing through said duct, second heater means mounted outside said duct for heating air circulating externally of said duct, and viscometer means mounted at least partially within said duct downstream of said heater means for measuring the viscosity of liquids in containers supported upon said support means.

2. The apparatus of claim 1 wherein said test chamber has a top wall, a bottom wall and side walls and wherein said second heating means is embedded within at least one of said walls.

3. The apparatus of claim 2 wherein said second heating means has a heating element embedded within said chamber top wall.

4. The apparatus of claim 2 wherein said second heating means has a heating element embedded within said chamber bottom wall.

5. The apparatus of claim 4 wherein said second heating means has a heating element within a said chamber top wall.

6. The apparatus of claim 2 wherein said chamber walls have a metallic inner shell and a thermally insulative outer shell and wherein said second heater means has a heating element mounted between said inner shell and said outer shell.

7. The apparatus of claim 1 wherein said duct has an inlet and an outlet, and wherein said air circulating means comprises a fan mounted adjacent said duct inlet.

8. The apparatus of claim 7 wherein said support means is mounted within said chamber adjacent said duct outlet.

9. The apparatus of claim 8 wherein said support means comprises a tray mounted below said duct outlet.

10. The apparatus of claim 9 wherein said support means further comprises means for repositioning said tray along a substantially horizontal plane located below said duct outlet.

11. The apparatus of claim 9 further comprising means for raising and lowering said viscometer means.

12. The apparatus of claim 1 further comprising thermal ballasting means mounted in said duct between said first heater means and said viscometer means.

13. The apparatus of claim 12 wherein said thermal ballasting means comprises a plurality of mutually spaced metallic plates.

14. A method of measuring the viscosity of a liquid in a container which comprises the steps of:

(a) placing the container in a thermally insulated chamber housing a duct and a viscometer mounted at least partially within the duct, (b) circulating air within the chamber through the duct over the viscometer, about the outside of the duct and back into the duct, (c) heating the air flowing internally within the duct with a first heater, (d) heating the air flowing externally of the duct within the chamber prior to re-entry of the air into the duct with a second heater, and (e) inserting the viscometer into the container and liquid.

* * * * *